(12) United States Patent
Wu et al.

(10) Patent No.: US 7,745,626 B2
(45) Date of Patent: Jun. 29, 2010

(54) STEREOSELECTIVE ALKYLATION OF CHIRAL 2-METHYL-4-PROTECTED PIPERAZINES

(75) Inventors: Wenxue Wu, West Windsor, NJ (US); Hongbiao Liao, Bridgewater, NJ (US); David J. Tsai, Warren, NJ (US); David R. Andrews, Maplewood, NJ (US); Dinesh Gala, East Brunswick, NJ (US); Gary M. Lee, Belmont, CA (US); Martin Lawrence Schwartz, Morris Plains, NJ (US); Timothy L. McAllister, Westfield, NJ (US); Xiaoyong Fu, Edison, NJ (US); Donal Maloney, Union, NJ (US); Tiruvettipuram K. Thiruvengadam, Kendall Park, NJ (US); Chou-Hang Tann, Berkeley Heights, NJ (US)

(73) Assignee: Schering Corporation, Kenilworth, NJ (US)

( * ) Notice: Subject to any disclaimer, the term of this patent is extended or adjusted under 35 U.S.C. 154(b) by 1361 days.

(21) Appl. No.: 11/089,858

(22) Filed: Mar. 25, 2005

(65) Prior Publication Data
US 2005/0171120 A1 Aug. 4, 2005

Related U.S. Application Data

(62) Division of application No. 10/400,429, filed on Mar. 27, 2003, now Pat. No. 6,872,826.

(60) Provisional application No. 60/368,707, filed on Mar. 29, 2002.

(51) Int. Cl.
*C07D 295/023* (2006.01)
(52) U.S. Cl. .................................... 544/386
(58) Field of Classification Search ................ 544/386
See application file for complete search history.

(56) References Cited

U.S. PATENT DOCUMENTS 6,391,865 B1 5/2002 Baroudy et al.

FOREIGN PATENT DOCUMENTS

WO WO 00/66558 11/2000

OTHER PUBLICATIONS

Tagat et al., "Piperazine-Based CCR5 Antagonists as HIV-1 Inhibitors. I: 2(S)-Methyl Piperazine as a Key Pharmacophore Element" *Bioorganic & Medicinal Chemistry Letters* 11:2143-2146(2001).
Camuzat-Dedenis et al., "Reaction of Phosphonium Ylides and Aromatic Nitriles under Lewis Acid conditions: an Easy Access to Aryl-Substituted α-Methoxyacetophenones" *Synthesis* (9):1558(1999).
Wang et al., "Regioselective Monobenzoylation of Unsymmetrical Piperazines", *J. Org. Chem.* 65: 4740-4742, (2000). XP-002260871.
Jacobson et al., "Piperazine Imidazo[1,5-a]quinoxaline Ureas as High-Affinity $GABA_A$ Ligands of Dual Functionality", *J. Med. Chem.* 42: 1123-1144, (1999). XP-002922740.
Beck et al., "Histamine Antagonists. IV. C-Methyl Derivatives of 1,4-Disubstituted Piperazines", *Journal of American Chemical Society* 74: 605-608, (1952). XP-002260872.
Bolos et al., "7-[3-(1-Piperidinyl)propoxy]chromenones as Potential Atypical Antipsychotics", *J. Med. Chem.* 39: 2962-2970, (1996). XP-002260873.
Manetti et al., "Molecular Simplification of 1,4-Diazabicyclo[4.3.0]nonan-9-ones Gives Piperazine Derivatives That Maintain High Nootropic Activity", *J. Med. Chem.* 43: 4499-4507, (2000). XP-002260874.
Tagat et al., "Piperazine-Based CCR5 Antagonists as HIV-1 Inhibitors. I: 2(S)=Methyl Piperazine as a Key Pharmacophore Element", *Bioorganic & Medicinal Chemistry Letters* 11: 2143-2146, (2001). XP-002246767.
Fujita et al., "Synthesis of Optically Active 5-Substituted-2-pyrrolidinone Derivatives Having Atropisomeric Structure and 3,5-*Cis*-Selective Reaction of Their Enolates with Electrophiles", *J. Org. Chem.* 65: 1108-1114, (2000). XP-002246768.
Lewis et al., "Molecular Photochemistry. XVIII. Type II Photoelimination and 3-Oxetanol Formation from ◊-Alkoxyacetophenones and Related Compounds", *Journal of Organic and Biological Chemistry* 92: 311-320, (1970). XP-002260875.

*Primary Examiner*—James O Wilson
*Assistant Examiner*—Ebenezer Sackey
(74) *Attorney, Agent, or Firm*—H. Eric Fischer; Gerard M. Devlin

(57) ABSTRACT

In an illustrative embodiment, the present invention describes the synthesis of the following compound and similar compounds, in high stereochemical purity by a novel stereoselective alkylation process:

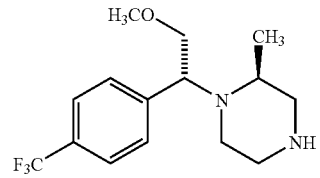

5 Claims, No Drawings

STEREOSELECTIVE ALKYLATION OF CHIRAL 2-METHYL-4-PROTECTED PIPERAZINES

RELATED APPLICATIONS

This application is a divisional of application U.S. Ser. No. 10/400,429, filed Mar. 27, 2003 now U.S. Pat. No. 6,872,826, now allowed and herein incorporated by reference, which in turn claims benefit under 35 USC 119(e) from provisional application U.S. Ser. No. 60/368,707, filed Mar. 29, 2002.

FIELD OF THE INVENTION

This application discloses stereoselective alkylation of chiral 2-alkyl-4-protected piperazines, with the reaction being catalyzed by inorganic bases. This application claims priority from U.S. provisional application, Ser. No. 60/368,707, filed Mar. 29, 2002.

BACKGROUND OF THE INVENTION

Stereoselective alkylation of chiral amines with an alkylating compound is an important reaction in organic synthesis. Generally, a suitable leaving group is placed on the alkylating compound which is then reacted with the chiral amine in the presence of a base. The base absorbs the by-product acid. Suitable leaving groups include moieties such as halide, mesylate, tosylate and the like. Typically, the base used is an organic base such as a tertiary amine. Examples of suitable organic bases are pyridine, triethylamine, N,N-diisopropylethylamine, 2,2,6,6-tetramethylpiperidine ("TMP") and the like. Thus, for example, J. Tagat et al, *Bioorg. Med. Chem.*, (2001) 11 2143-2146 describe the synthesis shown in Scheme 1, where TMP is used as the organic base in the alkylation reaction:

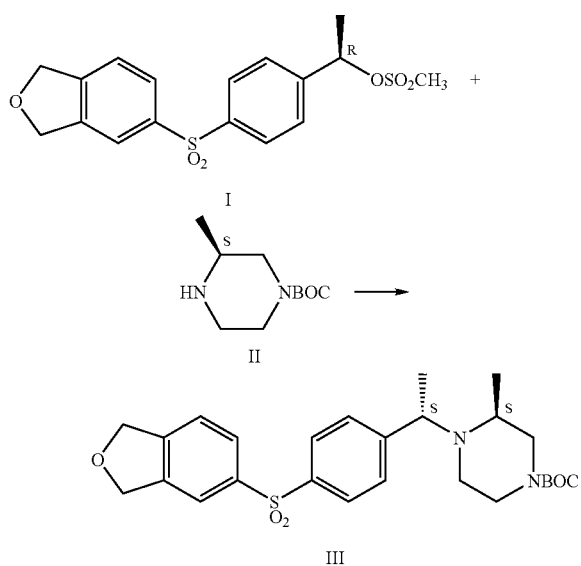

U.S. patent application Ser. No. 09/562,814, filed May 1, 2000, incorporated herein by reference (now U.S. Pat. No. 6,391,865), discloses the following reaction to prepare the compound of Formula VI. The compound of Formula VI is an intermediate in the synthesis of the compound of Formula VII which is also described in the above-noted

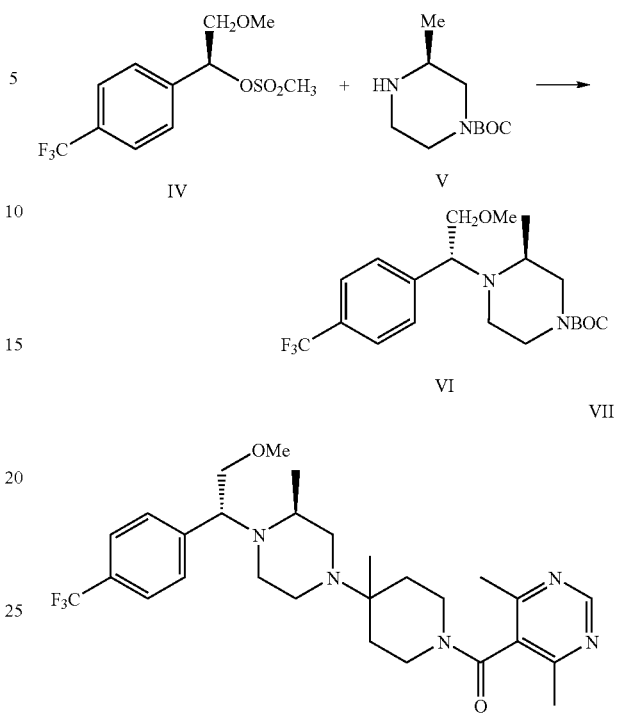

'814 patent application. The '814 patent application discloses the compound of Formula VII as an antagonist of the CCR5 receptor. Antagonists of the CCR5 receptor are known to be useful in the treatment of AIDS and related HIV infections. CCR-5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease. In view of the importance of antagonists of the CCR5 receptor, improved methods of making such antagonists and/or their intermediates are always of interest.

There are two important criteria in stereoselective alkylation of amines. It is important to obtain high yields of the desired product and it is important to produce the product in high chiral purity. Thus, for example, in the reaction depicted in Scheme 1, there are two chiral centers in the starting materials, with R and S configuration respectively. One would ideally like to obtain a high yield of the product compound of Formula III but also prefer to obtain the (S,S) in the product (in that particular reaction) to the highest extent possible. (One chiral center undergoes inversion during the reaction as indicated.) This can also be stated as high stereoselectivity or high selectivity ratio in the reaction. In reactions where an organic base is employed as the catalyst such as those described above in Scheme 1, yields of about 50-65% of the product is obtained with a selectivity ratio of 3:1 of the desired (S,S) isomer to the undesired (R,S) isomer. This necessitates further separation steps, adding to the cost. It will be desirable to obtain a higher selectivity of the desired iso-

SUMMARY OF THE INVENTION

In one embodiment, this invention teaches a stereoselective alkylation process for preparing a compound of Formula VIII:

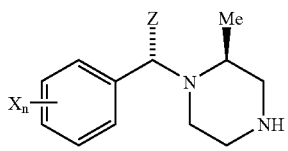

VIII wherein X is a substituent on the aromatic ring, n is an integer ranging from 1 to 5 and denotes the number of X moieties which may be the same or different each X being independently selected from the group consisting of alkyl, halogen, halogenated alkyl, alkoxy, aryl, aryloxy and heteroaryl; and Z is selected from the group consisting of alkyl, alkoxyalkyl, aryl, heteroaryl, heteroarylalkyl and arylalkyl;

said process comprising (a) reacting, in the presence of an inorganic catalyst in a solvent, a compound of Formula IX:

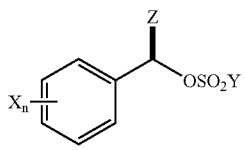

IX where X, n and Z are as defined above, and Y is selected from the group consisting of alkyl, halogenated alkyl, or aryl with said aryl being optionally substituted with alkyl, nitro or halogen;

with a compound of Formula X:

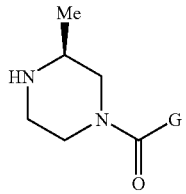

X where G is selected from the group consisting of alkyl, halogenated alkyl, alkoxy, aryl, aryloxy and arylalkoxy, and (b) removing the —C(O)-G group by treatment with an acid or a base.

The present process, when $Z=CH_2OMe$, by employing an inorganic catalyst instead of an organic base, surprisingly produces the desired compound of Formula VIII in high yields (which means at least 50% yields on a molar basis from the compound of Formula IX with high preferred stereochemical content (which in this instance means at least about a 2:1 molar ratio of R,S stereochemistry to S,S stereochemistry respectively). In fact, in most instances, as the EXAMPLES section shows, when $Z=CH_2OMe$, the present inventive process yielded a stereochemistry ratio of better than 90:10 of the R,S to the S,S respectively in the compound of Formula VIII. The denoted stereochemistry of R,S and S,S in Formula VIII assumes that Z has priority over the aryl in the naming convention. When Z=methyl, the desired as well as the obtained major isomer was S,S. When Z=methyl, the S,S and R,S stereochemistry in the compound of Formula VIII is depicted below, where the letters S and R indicate the stereochemistry at the respective chiral carbon atom indicated:

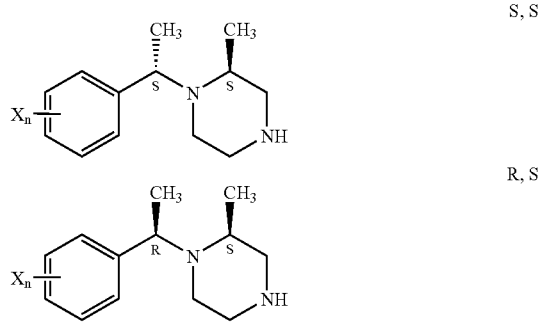

The inventive stereoselective alkylation of a chiral amine, especially a chiral 2-alkyl-4-protected piperazine, results in high yields and high stereoselectivity. As stated above, the compounds represented by Formula VIII are desired intermediates for the preparation of CCR5 receptor antagonists. Thus, the present invention affords an efficient process to prepare such CCR5 antagonists.

In another embodiment, the present invention discloses a novel process to selectively prepare a mono-4-protected 2-methylpiperazine from its corresponding 2-methylpiperazine in high yields, said process comprising reacting said 2-methylpiperazine with about a molar equivalent of a protecting reagent in a solvent, with the reaction being catalyzed by an acid catalyst or a base catalyst. An example of such mono-4-protected 2-methylpiperazine is the compound of Formula X. The term "selectively prepare" refers to the preparation of a 4-protected 2-methylpiperazine with at least about a 80% preferential regiospecificity of protection at the 4-position over that at both the 1- and 4-positions, and at least 95% preferential protection at the 4-position over that at the 1-position.

DETAILED DESCRIPTION

In one embodiment, the present invention discloses a novel, easy-to-use process for preparing a compound of Formula VIII in high yields and high stereochemical purity. In another embodiment, it discloses a novel process to selectively monoprotect the nitrogen atom at the 4-position of a 2-methylpiperazine.

The inventive process to prepare the compound of Formula VIII is illustrated below where the compound of formula VIII has the definitions $X=CF_3$, n=1, Y and G are defined above, and $Z=-CH_2-OCH_3$:

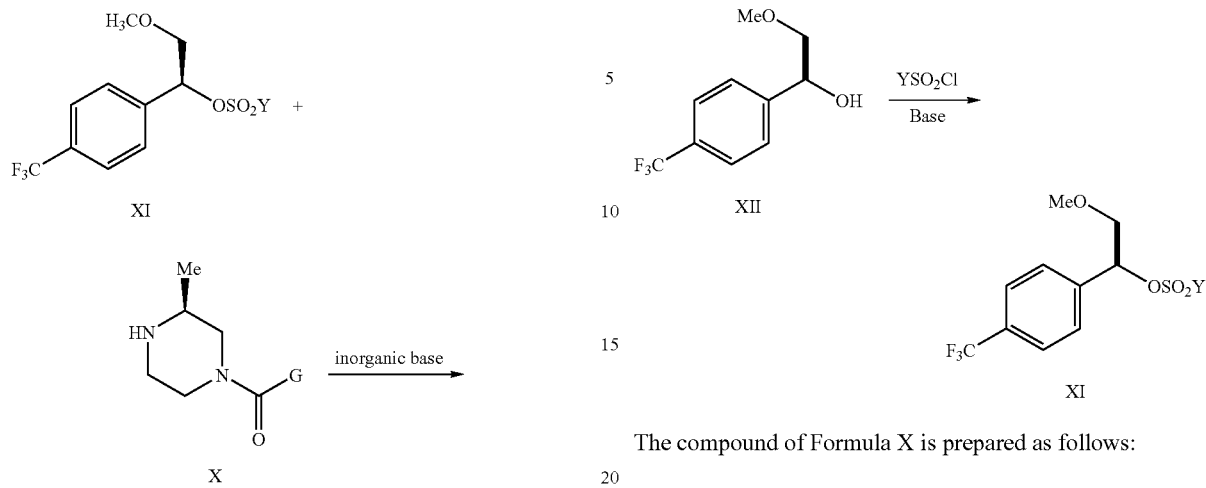

The compound of Formula XI is prepared as follows:

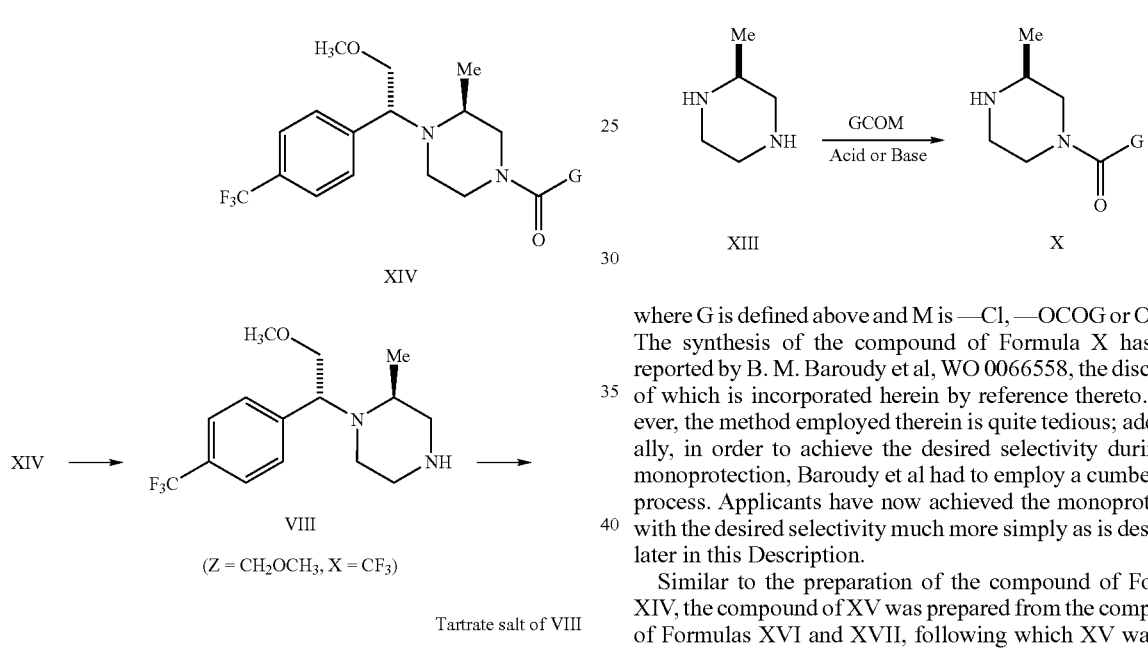

The compound of Formula X is prepared as follows:

where G is defined above and M is —Cl, —OCOG or $OC_2H_5$. The synthesis of the compound of Formula X has been reported by B. M. Baroudy et al, WO 0066558, the disclosure of which is incorporated herein by reference thereto. However, the method employed therein is quite tedious; additionally, in order to achieve the desired selectivity during the monoprotection, Baroudy et al had to employ a cumbersome process. Applicants have now achieved the monoprotection with the desired selectivity much more simply as is described later in this Description.

Similar to the preparation of the compound of Formula XIV, the compound of XV was prepared from the compounds of Formulas XVI and XVII, following which XV was converted to an analog of the compound of VIII where Z is now methyl:

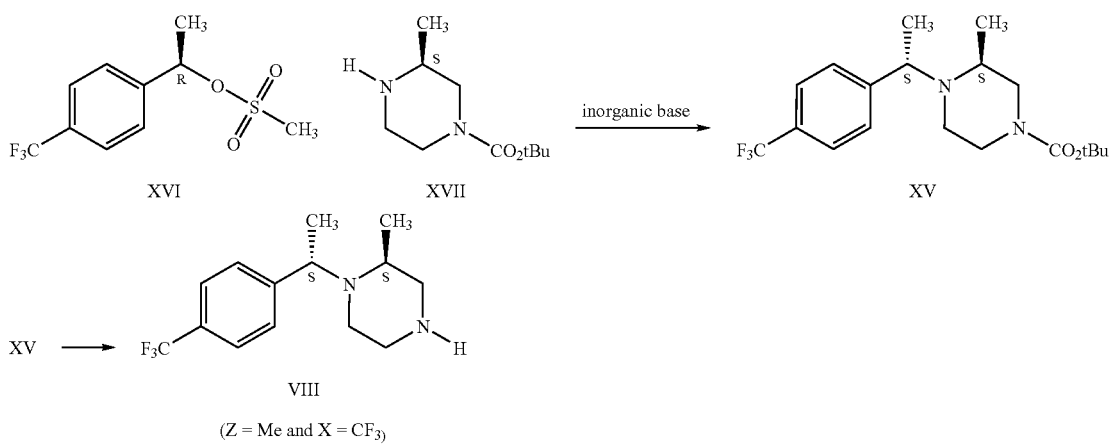

Again, as in the case of the preparation of the compound of Formula XIV, an inorganic base was used in the above-noted reaction to prepare the compound of Formula XV and found to offer significant advantages over the use of an organic base, in terms of yields and stereochemical content. The compounds of Formulas XVI and Formula XVII were prepared as described by B. M. Baroudy et al, WO 0066558. Details are in provided in the Examples section below.

While the preferred reagents and reaction conditions for the various steps in the inventive process are described in detail in the Examples section, the following summarizes the details.

As used above, and throughout the specification, the following terms, unless otherwise indicated, shall be understood to have the following meanings:

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, —N(cycloalkyl)$_2$, —NH(aryl), —N(aryl)$_2$, carboxy and —C(O)O-alkyl. Non-limiting examples of suitable alkyl groups include methyl, ethyl, n-propyl, isopropyl, n-butyl, t-butyl, n-pentyl, trifluoromethyl, benzyl and cyclopropylmethyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl, tolyl, chlorophenyl, and naphthyl.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, phenethyl and naphthlenylmethyl. The bond to the parent moiety is through the alkyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, quinolinyl, pyrazolyl, imidazolyl, thienyl, pyrimidinyl, isoxazolyl, oxazolyl, thiazolyl and the like.

"Halo" means fluoro, chloro, bromo, or iodo groups. Preferred are fluoro, chloro or bromo, and more preferred are bromo and chloro.

"Halogen" means fluorine, chlorine, bromine, or iodine. Preferred are fluorine, chlorine or bromine, and more preferred are bromine and chlorine.

"Acyl" means an alkyl-C(O)— group or an aryl-C(O)— group in which the alkyl and aryl are as previously described. The bond to the parent moiety is through the carbonyl. Preferred acyls contain a lower alkyl. Non-limiting examples of suitable acyl groups include acetyl, propanoyl and butanoyl and benzoyl.

"Alkoxy" means an alkyl-O— group in which the alkyl group is as previously described. Non-limiting examples of suitable alkoxy groups include methoxy, ethoxy, n-propoxy, isopropoxy, benzyloxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkoxycarbonyl" means —C(O)O-alkyl, wherein the alkyl is as previously described. Non-limiting examples include methoxycarbonyl, ethoxycarbonyl, benzyloxycarbonyl and the like.

The term "halocarbonyloxyalkyl" refers to groups such as alkyl-O—C(O)-halo, for example, alkyl chloroformate, e.g. ethyl chloroformate, benzyl chloroformate and the like.

"Ring system substituent" means a substituent attached to an aromatic or non-aromatic ring system which, for example, replaces an available hydrogen on the ring system. Ring system substituents may be the same or different, each being independently selected from the group consisting of alkyl, aryl, heteroaryl, aralkyl, alkylaryl, heteroaralkyl, alkylheteroaryl, hydroxy, hydroxyalkyl, alkoxy, aryloxy, acyl, aroyl, halo, nitro, cyano, carboxy, alkoxycarbonyl and aryloxycarbonyl.

In order to prepare the compound of Formula XI, the compound of Formula XII is reacted with a sulfonyl chloride of formula YSO$_2$Cl in the presence of a suitable base. A solvent may optionally be employed in the reaction. Non-limiting examples of YSO$_2$Cl include methane sulfonyl chloride, trifluoromethyl sulfonyl chloride, nanofluorobutyl sulfonyl chloride, 2,2,2-trifluoroethyl sulfonyl chloride, benzene sulfonyl chloride, p-toluene sulfonyl chloride, 4-nitrophenyl sulfonyl chloride, 4-bromo sulfonyl chloride, 4-chlorophenyl sulfonyl chloride and the like. Methane sulfonyl chloride, p-toluenesulfonyl chloride and 4-chlorophenyl sulfonyl chloride are most preferred. Non-limiting examples of suitable bases include, for example, diazabicyclo[2,2,2]octane ("DABCO"), pyridine, triethylamine, similar tertiary amines and the like. Non-limiting examples of suitable optional solvents include, for example, hydrocarbon, pyridine, nitrile, ether, ketone, ester and the like, with hydrocarbon being preferred, and toluene and xylene being most preferred. The solvent may be used generally in about 1 to about 50 times the molar amounts of the starting compound, preferably in about 2 to about 20 times and typically in about 5 to about 15 times. The sulfonyl chloride may be used generally in about 1 to about 5 molar equivalents with respect to the starting compound, preferably in about 1 to about 2 molar equivalents, and typically in about 1 to 1.5 molar equivalents. The base may be used generally in about 1 to about 10 molar equivalents of the starting compound, preferably in about 1 to about 5 molar equivalents, and typically in about 1 to about 2 molar equivalents.

The compound of Formula XII may be dissolved, dispersed, suspended or otherwise suitably distributed in a mixture containing the solvent and base (or the base only if the base itself is the solvent), and the reaction mixture stirred or otherwise suitably mixed to facilitate the reaction. The reaction may be performed generally at about −10° C. to about 50° C., preferably at about −10° C. to about 40° C. and most preferably at about −5° C. to about 20° C., for about 0.5 to about 10 hours generally, about 0.5 to about 5 hours preferably and about 1 to about 3 hours most preferably. The product of Formula XI may be isolated and purified by methods well known to those skilled in the art of preparing sulfonates. If pure enough, it may be subjected to the next stage of the reaction sequence directly without a separate purification.

The compound of Formula X is prepared from a compound of Formula XIII which is commercially available as well as its salt. The preparation of the compound of Formula XIII is also reported in the above-noted B. M. Baroudy et al, WO 0066558. The compound of Formula XIII may be mono-4-protected by reacting with the compound GCOM (where G is as defined above) under base catalysis or acid catalysis. For a base catalyzed reaction, inorganic bases such as, for example, potassium carbonate, sodium bicarbonate and the like, or organic bases such as, for example, pyridine, triethylamine, DABCO, N,N-diisopropylethylamine and the like, or mixtures thereof, may be employed. The base may be employed generally in about 1-10 molar equivalents, preferably in about 1-5 molar equivalents and typically in about 1-2 molar equivalents with respect to the compound of Formula XIII. A solvent may be used unless, as described above, the base itself may act as the solvent. Non-limiting examples of suitable solvents include, for example, hydrocarbons (such as toluene, xylene, heptane and the like), ethers (such as, for example, THF, 1,4-dioxane and the like), alcohols (such as, for example, methanol, ethanol and the like), ketones (such as, for example, acetone, methyl ethyl ketone and the like) or mixtures thereof. About 1 molar equivalent of the compound of Formula GCOM is used in the reaction. Carboxylic esters are examples of suitable GCOM useful in the reaction such as, for example, ethyl trifluoroacetate, and the like.

The compound of Formula XIII may be dissolved or otherwise suitably distributed in the mixture of the solvent and the base (or base only if the base itself is the solvent), GCOM may be added and suitably mixed to let the reaction proceed to desired completion. The reaction may be performed generally in temperature ranges of about −10° C. to about 50° C., preferably at about −10° C. to about 40° C. and most preferably at about −5° C. to about 30° C., for about 0.5 to about 60 hours generally, about 1 to about 50 hours preferably and about 1 to about 40 hours most preferably. The product of Formula X may be isolated and purified by methods well known to those skilled in the art. It may be analyzed for regiospecificity and chemoselectivity using analytical techniques such as, for example, NMR and HPLC, as is well known to those skilled in the art. In a typical example, where GCOM was ethyl trifluoroacetate, an 85% yield of a mixture of 4-trifluroacetyl-2-methyl-piperazine and 1,4-bis(trifluoroacetyl)-2-methyl-piperazine (88:12 molar ratio) was obtained. Such a preferred chemoselectivity of mono-N-protection (essentially free of the N,N-diprotection) in a reaction involving a 2-methylpiperazine is advantageous commercially. Additionally, the regioisomer, of 1-trifluroacetyl-2-methyl-piperazine, was not detected. Thus, the reaction was substantially and almost completely regiospecific (meaning position 4 versus position 1).

The reaction of the compound of Formula XIII with GCOM may be catalyzed by acid instead of by a base. Suitable acids are preferably weak acids and include, for example, acetic acid, propionic acid, benzoic acid, oxalic acid, citric acid and the like, and mixtures thereof. The acid may be employed in about 1-10 molar equivalents generally, 1-6 molar equivalents preferably and 2-4 molar equivalents typically, based on the compound of Formula XIII. A solvent may optionally be employed. Nonlimiting examples of suitable solvents include, for example, water, alcohols (such as, for example, methanol, ethanol, isopropanol and the like), dimethylsulfoxide, ethers (such as, for example, THF, 1,4-dioxane) and mixtures thereof. Preferred solvents are water alone or in admixture with an alcohol and/or an ether. Examples of GCOM useful in the reaction include carboxylic esters (such as, for example, acid chlorides (e.g. acetyl chloride, benzoyl chloride and the like), acid anhydrides (such as, for example, acetic anhydride, di-t-butyl dicarbonate or

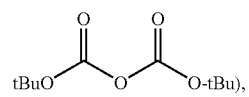

halocarbonyloxyalkyl compounds (such as, for example, methyl chloroformate, ethyl chloroformate, benzyl chloroformate) and the like. The compound of Formula XIII may be dissolved or otherwise suitably distributed in a mixture of the solvent and the acid, GCOM may be added and suitably mixed to let the reaction proceed to desired completion. The reaction may be performed generally in the temperature ranges of about −10° C. to about 50° C., preferably at about −10° C. to about 40° C. and most preferably at about −5° C. to about 30° C., for about 0.5 to about 15 hours generally, about 0.5 to about 10 hours preferably and about 0.5 to about 5 hours most preferably. The product of Formula X may be isolated and purified by methods well known to those skilled in the art. It may be analyzed for regiospecificity and chemoselectivity using analytical techniques such as, for example, NMR and HPLC, as is well known to those skilled in the art. In a typical example, where GCOM was benzyl chloroformate, an 89% yield of a product containing more than 98 molar percent of 4-benzyloxycarbonyl 2-methyl piperazine was obtained. Additionally, only 0.5% of the regioisomer, 1-benzyloxycarbonyl-2-methyl piperazine, was detected. Again, such a high regiospecificity and chemoselectivity of mono-N-protection in a reaction involving a 2-methylpiperazine are surprising.

The compounds of Formulas XI and X may then be reacted in the presence of an inorganic base to obtain the compound of Formula XIV (where X=CF$_3$, n=1 and Z=—CH$_2$—OCH$_3$) in high yields and high stereochemical purity. (This reaction incidentally is also a stereoselective alkylation of the amine of Formula X using the alkylating agent of Formula XI.) The compounds of Formulas XI and X are dissolved, suspended or otherwise suitably distributed in a solvent which contains an inorganic base, preferably in a finely divided form. The mixture is agitated to let the reaction proceed to completion. Nonlimiting examples of suitable solvents include, for example, hydrocarbons (such as toluene, xylene, heptane and the like), ethers (such as, for example, THF, 1,4-dioxane and the like), ketones (such as, for example, acetone, methyl ethyl ketone and the like), esters (such as, for example, ethyl acetate, isopropyl acetate and the like), nitriles (such as, for example, acetonitrile and the like), amides (such as, for example, N,N-dimethylformamide, N,N-dimethylacetamide, N-methylpyrrolidinone and the like), dimethylsulfoxide, and mixtures thereof. Nonlimiting examples of suitable inorganic catalysts include, for example, a carbonate, bicarbonate, phosphate, borate, sulfite and mixtures thereof. Specific catalysts include, for example, K$_2$CO$_3$, NaHCO$_3$, Na$_3$PO$_4$, CaCO$_3$, Na$_2$BO$_3$ and K$_2$SO$_3$ and mixtures thereof. About 1:1 to about 1:5 (preferably about 1:2) molar equivalents of the compounds of Formulas XI and X are used in the reaction. The reaction may be performed generally in temperature ranges of about 10° C. to about 130° C., preferably at about 50° C. to about 110° C. and most preferably at about 80° C. to about 110° C., for about 0.5 to about 60 hours generally, about 5 to about 50 hours preferably and about 10 to about 40 hours most preferably. The product of Formula XIV may be isolated and purified by methods well known to those skilled in the art. It may be analyzed for stereoselectivity using analytical techniques such as, for example, NMR, HPLC and the like, as is well known to those skilled in the art.

Several illustrative preparations are detailed in the EXAMPLES section below. In a typical reaction where the starting compound of Formula XI had a S/R stereochemistry ratio of 96.4:3.6 (mole:mole), a product of the Formula XIV ((where X=CF$_3$, n=1 and Z=—CH$_2$—OCH$_3$) was obtained in about 85% yield with a RS/SS stereochemistry ratio of about 95.9:4.1. Such a high stereochemical purity in the N-alkylation of amines in general, and 2-methylpiperazines in particular, has commercial advantages. For comparison, essentially the same reaction was run using an organic base, diisopropylethylamine, instead of the inorganic base. A 58.3% yield of the alkylated compound XIV with a stereochemistry ratio (RS/SS) of 82.7/17.3 was obtained, substantially inferior to the present invention using inorganic base.

The compound of Formula XIV is then converted to the compound of Formula VIII by reacting it in a suitable manner such as, for example, treatment with an acid (such as, for example, HCl, H$_2$SO$_4$ and the like), or a base (such as, for example, NaOH, KOH and the like) to remove the —C(O)—G moiety. The compound of Formula VIII may then optionally be converted into a suitable salt by reacting with a suitable acid as is well known to those skilled in the art. Suitable salts are, for example, tartrate, oxalate, fumarate, maleate, hydrochloride and the like.

The products of the various steps in the reaction schemes described herein may be isolated and purified by conventional techniques such as, for example, filtration, recrystallization, solvent extraction, distillation, precipitation, sublimation, chromatography and the like, as is well known to those skilled in the art. The products may be analyzed and/or checked for purity by conventional methods such as, for example, thin layer chromatography, NMR, HPLC, melting point, mass spectral analysis, elemental analysis and the like, as is well known to those skilled in the art.

The following nonlimiting EXAMPLES are provided in order to further illustrate the present invention. While the EXAMPLES are described herein as the preparation of the compound of Formula VIII (where X=CF$_3$, n=1 and Z=—CH$_2$—OCH$_3$ or Z=CH$_3$), it will be apparent to those skilled in the art that many modifications, variations and alterations to the present disclosure, both to materials, methods and reaction conditions, may be practiced. All such modifications, variations and alterations are intended to be within the spirit and scope of the present invention.

EXAMPLES

Unless otherwise stated, the following abbreviations have the stated meanings in the Examples below:

HPLC=High Performance Liquid Chromatography m.p: melting point b.p.: boiling point mm: millimeter NMR=nuclear magnetic resonance spectroscopy DMSO=dimethylsulfoxide THF=Tetrahydrofuran mL=milliliters g=grams rt or r.t.=room temperature (ambient)

dr: diastereomeric ratio

In the following Examples, yields in the various reactions are quoted on molar basis, and the RS/SS or SS/RS ratio is quoted as a molar ratio.

Example 1

Preparation of Compound of Formula X (G=CF$_3$) from S-2-methylpiperazine (Base Catalyzed) (Highly Regioselective Mono-N-Protection)

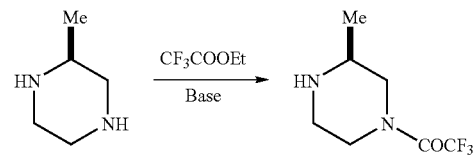

To a mixture of (S)-2-methylpiperazine (20 g, from Deepwater Chemicals, Woodward, Okla.) and potassium carbonate (extra fine, 55.2 g) in 200 mL THF was added ethyl trifluoroacetate (119 mL) at 0° C. over 1 h. The mixture was stirred at 0° C. for 18 h and then at r.t. overnight. Solids were removed by filtration and the filtrate was concentrated. HPLC analysis showed that 33.5 g product was contained in the filtrate (85% yield). The mono-protection to di-protection product ratio was about 88:12.

The product can be purified by column chromatography (gradient elution, initial solvent composition: 40% heptane, 40% ethyl acetate, and 20% isopropanol; final solvent composition: 60% ethyl acetate, 40% isopropanol). Yellow oil. $^1$H NMR (D$_2$O): 4.41 (m, 1H), 3.85 (m, 1H), 3.23 (m, 0.5H, one rotamer), 3.09 (m, 1H), 2.86 (m, 3H), 2.51 (t, J=11.8 Hz, 0.5H, the other rotamer), 1.99 (br S., 1H), 1.14 (split d, J=6.3 Hz, 3H).

The regiochemistry was confirmed by converting the crude product to 1-t-butoxycarbonyl-4-trifluoroacetyl-2-methylpiperazine. Its regioisomer, 4-t-butoxycarbonyl-1-trifluoroacetyl-2-methylpiperazine was not detected by $^{19}$F NMR (CDCl$_3$, 1-t-butoxycarbonyl-4-trifluoroacetyl-2-methylpiperazine: −68.63, −69.29; 4-t-butoxycarbonyl-1-trifluoroacetyl-2-methylpiperazine: −69.42, −69.44).

Example 2

Preparation of Compound of Formula X (G=OBn) from S-2-methylpiperazine (Acidic Catalysis) (Highly Regioselective Mono-N-Protection)

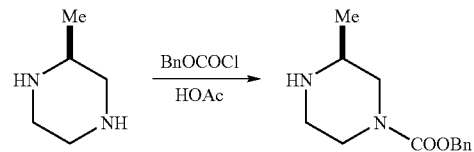

To a solution of S-2-methylpiperazine (100 g) in methanol (1200 mL) and water (400 mL) was charged 180 mL acetic acid. Benzyl chloroformate was added over a period of 90 min at about 0-10° C. After agitation at about 0-10° C. for 1 h, the reaction mixture was diluted with water and mixture was concentrated to remove methanol. HPLC analysis showed that the ratio of mono-acylation vs. di-acylation products was about 98/2. The resulting aqueous mixture was washed with toluene (300 mL). The aqueous layer was basified with 25% NaOH (690 mL) and extracted with toluene (700 mL). The toluene layer was concentrated and residual solid sodium acetate was removed by filtration. HPLC analysis showed that the concentrate contained 208 g product (89% yield). The product thus prepared is very clean and can be used in the next step without further purification. HPLC analysis showed that the sample contained about 0.5% regioisomer (1-benzyloxy-carbonyl-2-methylpiperazine).

Pure S-4-benzyloxycarbonyl-2-methylpiperazine can be obtained by vacuum distillation (clear oil, b.p. 136° C./1 mm). $^1$H NMR (CDCl$_3$): 7.31 (m, 5H), 5.09 (m, 2H), 3.98 (m, 2H), 2.84 (m, 4H), 2.47 (m, 1H), 1.78 (br s, 1H), 1.00 (d, J=5.5 Hz, 3H).

Example 3-6

Preparation of Compound of Formula X from S-2-methylpiperazine: Compounds of Formula X were Prepared Using Similar Procedures to Example 2

| Example | G | Acylating Reagent | Solvent | Mono/Di Acylation | Yield % |
|---|---|---|---|---|---|
| 3 | Me | Ac$_2$O | Water | 96/4 | 74 |
| 4 | Ph | PhCOCl | THF/water | 94/6 | 77 |
| 5 | EtO | EtOCOCl | MeOH/water | 97/3 | 88 |
| 6 | t-BuO | Boc$_2$O | MeOH/water | 97/3 | 92 |

Physical and spectral data for compounds of Formula X:

G=Me (Example 3): very hygroscopic solid, b.p.: ~100° C./10 mm Hg. $^1$H NMR (D$_2$O): 4.21 (m, 1H), 3.84 (m, 1H), 2.55-3.40 (m, 5H), 2.02 (split s, 3H), 1.11 (split d, J=6.4 Hz, 3H).

G=Ph (Example 4): clear oil. $^1$H NMR (D$_2$O): 7.38 (m, 3H), 7.27 (d, J=7.1 Hz, 2H), 4.29 (m, 1H), 3.54 (m, 1H), 3.07 (m, 1H), 2.60-3.0 (m, 4H), 1.05, 0.84 (split d, J=6.3 Hz, 5.5 Hz, 3H).

G=OEt (Example 5): clear oil, b.p.: 130° C./15 mm Hg. $^1$H NMR (CDCl$_3$): 4.00 (q, J=7.0 Hz, 2H), 3.89 (br s, 2H), 2.84 (br d, J=9.4 Hz, 1H), 2.64 (m, 3H), 2.32 (br s, 1H), 1.64 (s, 1H), 1.13 (t, J=7.1 Hz, 3H), 0.93 (t, J=6.3 Hz, 3H).

G=O-t-Bu (Example 6): pale yellow solid, m.p.: 39° C.; b.p.: 95° C./0.5 mm Hg. $^1$H NMR (CDCl$_3$): 3.95 (br s, 2H), 2.98 (br d, J=9.6 Hz, 1H), 2.75 (m, 3H), 2.42 (br s, 1H), 2.38 (br s, 1H), 1.47 (s, 9H), 1.08 (d, J=6.3 Hz, 3H).

Example 7

Preparation of Compound of Formula X (G=O-t-Bu) from S-2-methylpiperazine (Traditional Method): Using essentially the same procedure as in Example 2 except that acetic acid was replaced by triethylamine and the reaction was carried out at −10° C. The mono-acylation/di-acylation ratio was found to be 82/18 by HPLC analysis.

Example 8

Preparation of the Compound of Formula XII from 4-Trifluromethyl Methoxyacetophenone

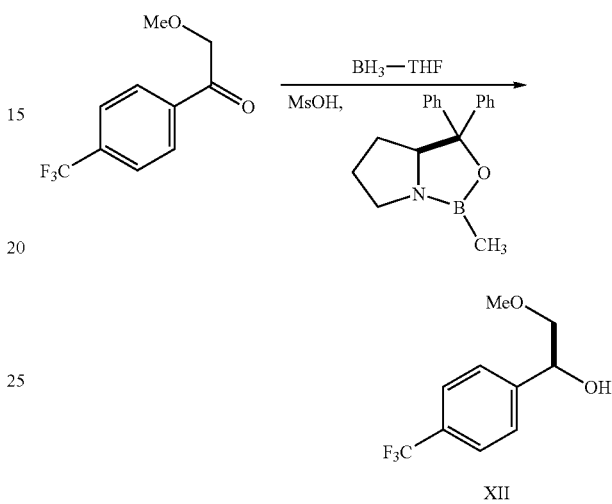

The compound of Formula XII was prepared by following a procedure similar to B. M. Baroudy et al., referred to above. The starting ketone, 4-trifluoromethyl methoxyacetophenone, was prepared by a literature procedure (Camuzat-Dedenis, B. et al, *Synthesis*, 1999, 1558). [4-Trifluoromethyl methoxyacetophenone (or 2-Methoxy-1-[4-(triflouromethyl) phenyl]ethanone) could also be prepared by a process described in Example 8A below.] To a solution of borane-THF complex (36.6 mL, 1.0 M solution in THF) in 50 mL toluene was slowly added methanesulfonic acid (0.15 mL) at r.t. After the mixture was stirred at r.t. for 10 minutes, (S)-2-methyl-CBS-oxazaborolidine (Callery Chemical Company, Evans City, Pa., 1.34 mL, 1.0 M solution in toluene) was added. After mixture was agitated at r.t. for 30 minutes, a solution of 4-trifluoromethyl methoxyacetophenone (10.0 g) in 30 mL toluene was added over 1 h at 20-30° C. After being stirred at r.t. for 1 h, the mixture was quenched with methanol (10 mL) at 10-20° C. This mixture was stirred at r.t. for 1 h, concentrated under vacuum to about 20 mL, and diluted with 80 mL toluene. This mixture was washed with 0.5 M sulfuric acid (30 mL, phase separation was aided by filtration through Celite). The organic layer was washed by saturated sodium bicarbonate (30 mL) followed a wash by water (30 mL). The organic layer was then concentrated and could be used directly in the next step. HPLC analysis showed that the concentrate contained 10.1 g of the compound of formula XII (99.6% yield of both enantiomers). The enantiomeric ratio (S/R) was 98.2/1.8. An analytical pure sample can be obtained by column chromatography (20% ethyl acetate/heptane). $^1$H NMR (CDCl$_3$) 7.63 (d, J=8.2 Hz, 2H), 7.53 (d, J=8.5 Hz, 2H), 4.97 (dd, J$_1$=6.6 Hz, J$_2$=1.2 Hz, 1H), 3.59 (dd, J$_1$=9.7 Hz, J$_2$=3.3 Hz, 1H), 3.46 (s, 3H), 3.43 (dd, J$_1$=9.7 Hz, J$_2$=8.7 Hz, 1H).

Example 8A

Preparation of 4-Trifluoromethyl methoxyacetophenone (or 2-Methoxy-1-[4-(triflouromethyl)phenyl]ethanone)

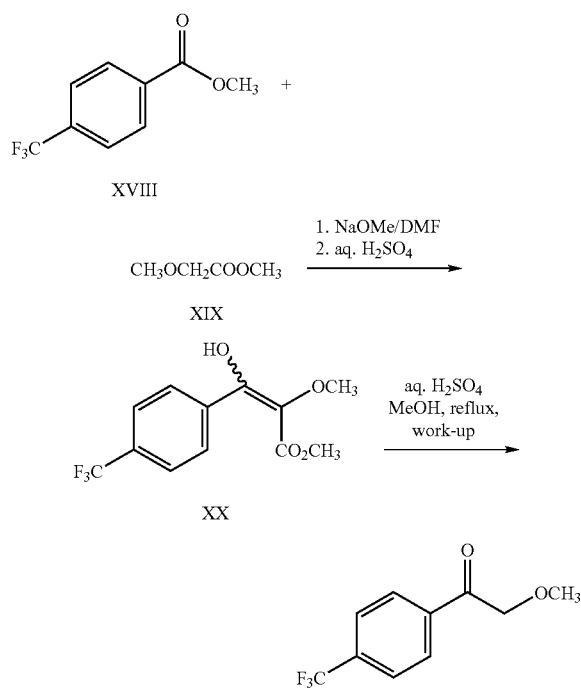

To a mixture of sodium methoxide (34.8 g) and methyl 4-(trifluoromethyl)benzoate (51.6 g) in 254 mL DMF was added methyl methoxyacetate (52.5 g) at −10° C. over 5 hr. The reaction mixture was stirred at −10° C. for 21 hr and quenched into a mixture of 2.3 M sulfuric acid (410 mL) and MTBE (185 mL) cooled to −8.5° C. The mixture was warmed to r.t., the layers were separated, the aqueous layer was extracted with MTBE (185 mL) and the combined organic layer back-washed with water (100 mL). HPLC analysis showed the crude Claisen product contained a mixture of keto, Z and E-enol tautomers, methyl 4-(trifluoromethyl)benzoate and 4-(trifluoromethyl)benzoic acid. The solvent was exchanged with methanol (350 mL) by distillation, 6 M sulfuric acid (180 mL) was added and the mixture was refluxed for 5 hr. HPLC analysis showed the mixture contained 44.4 g of product (82% overall yield), methyl 4-(trifluoromethyl)benzoate and 4-(trifluoromethyl)benzoic acid. Water (180 mL) was added, the mixture was distilled to approximately 450 mL and cooled to 10° C. as the product crystallized. The solids were filtered, washed with water (100 mL) and sucked dry to give the crude product. The crude product was taken up in MTBE (300 mL), washed with 5% sodium bicarbonate (100 mL) and 0.01% sulfuric acid (100 mL). The solvent was exchanged with heptane (200 mL) by distillation and chilled to −10° C. as the pure product crystallized. The pure product was isolated as pale yellow crystals (33.8 g, 61% yield, m.p.: 52° C.). $^1$H NMR (CDCl$_3$): 8.07 (d, J=8.2 Hz, 2H), 7.76 (d, J=8.3 Hz, 2H), 4.72 (s, 2H), 3.53 (s, 3H).

Example 9

Preparation of Compound of Formula XI from Compound of Formula XII (Y=4-chlorophenyl)

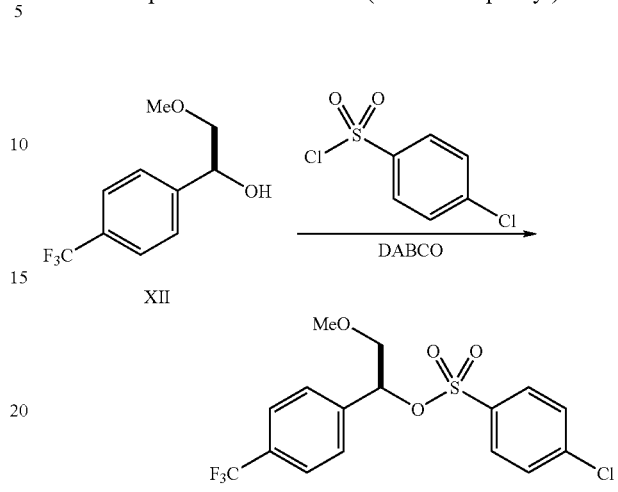

To a solution of the compound of Formula XII (300 g) and 1,4-diazabicyclo[2,2,2]octane (214 g) in 1500 mL toluene was added a solution of 4-chlorobenzenesulfonyl chloride (345 g) in 1500 mL toluene at a temperature between −5 to −15° C. over 1 h. The reaction mixture was stirred at −5 to −15° C. for 1 h and quenched with water (1500 mL). The biphasic mixture was stirred at r.t. for 2 h, settled, and the aqueous layer split off. The organic layer was washed with 0.5 M sulfuric acid (1500 mL) followed by saturated sodium bicarbonate (1500 mL). The crude product was isolated by vacuum concentration. The crude material could be used directly in the following step. Alternatively, it could be recrystallized from toluene/heptane. The pure product was isolated as pale yellow crystals (508.5 g, 94% yield, m.p.: 88.9° C.). $^1$H NMR (CDCl$_3$): 7.73 (m, 2H), 7.56 (d, J=8.3 Hz, 2H), 7.39 (m, 4H), 5.64 (dd, J$_1$=7.3, J$_2$=4.2, 1H), 3.73 (dd, J$_1$=11.1, J$_2$=7.4, 1H), 3.60 (dd, J$_1$=11.1, J$_2$=4.3, 1H), 3.31 (s, 3H).

Example 10

Preparation of Compound of Formula XI (Y=4-methylphenyl) from Compound of Formula XII: This compound was prepared following a similar procedure to Example 9. Yield: 92% after recrystallization (pale yellow solid). $^1$H NMR (CDCl$_3$): 7.64 (d, J=8.3 Hz, 2H), 7.50 (d, J=8.2 Hz, 2H), 7.33 (d, J=8.1 Hz, 2H), 7.19 (d, J=8.2 Hz, 2H), 5.60 (dd, J$_1$=6.9, J$_2$=4.6, 1H), 3.73 (dd, J$_1$=11.0, J$_2$=7.0, 1H), 3.60 (dd, J$_1$=11.0, J$_2$=4.6, 1H), 3.32 (s, 3H), 2.39 (s, 3H).

Example 11

Preparation of Compound of Formula XI (Y=Me) from Compound of Formula XII: This compound was prepared by following a procedure similar to B. M. Baroudy et al., stated above. $^1$H NMR (CDCl$_3$): 7.69 (d, J=8.2 Hz, 2H), 7.55 (d, J=8.1 Hz, 2H), 5.76 (dd, J$_1$=8.2 Hz, J$_2$=3.5 Hz, 1H), 3.77 (dd, J$_1$=11.1 Hz, J$_2$=8.2 Hz, 1H), 3.64 (dd, J$_1$=11.1 Hz, J$_2$=3.5 Hz, 1H), 3.45 (s, 3H), 3.04 (s, 3H).

Example 12

Preparation of Compound of Formula XIV (G=OBn) from Compound of Formula XI (Y=4-Chlorophenyl) (Stereoselective Alkylation)

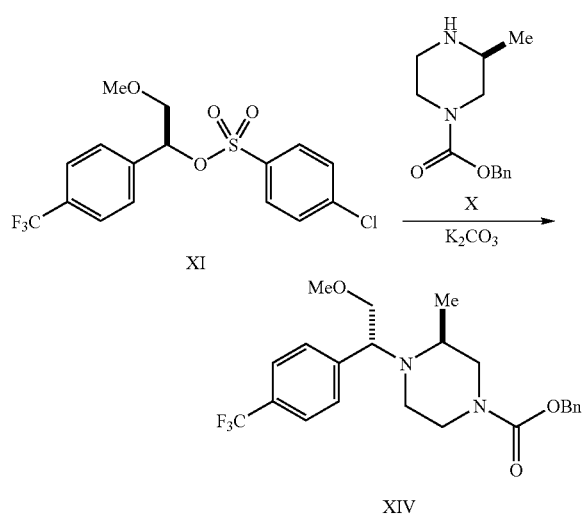

XI

XIV

The compound of Formula XI (Y=4-chlorophenyl, 20.0 g, S/R ratio: 96.4/3.6) and the compound of Formula X (G=OBn, 16.6 g) were mixed in a mixture of toluene (40 mL) and acetonitrile (40 mL) containing extra-fine potassium carbonate (14.0 g). This slurry was heated at 80-85° C. for 30 h and cooled. Solids were filtered and the filtrate was concentrated. HPLC analysis of the concentrate showed the presence of 18.7 g product (85% yield, RS/SS ratio: 95.9/4.1). The product can be isolated as an HCl salt. $^1$H NMR (DMSO-$d_6$): 11.90, 11.51 (split br s, 1H), 8.07 (br s, 1H), 8.01 (br d, J=6.6 Hz, 1H), 7.86 (br d, J=7.4 Hz, 2H), 7.37 (br m, 5H), 5.29, 4.69 (split br s, 1H), 5.11 (split br m, 2H), 3.00-4.30 (br m, 7H), 3.30 (s, 3H), 1.44, 1.36 (split br s, 3H).

Example 13

Preparation of Compound of Formula XIV (G=OBn) from Compound of Formula XI (Y=4-chlorophenyl) using an Organic Base (Comparative Example): The procedure is essentially the same as in Example 12 except that an organic base, diisopropylethylamine, was used. Yield: 58.3% and diastereomeric ratio (RS/SS) was 82.7/17.3, demonstrating the inferiority of this process (organic base) as compared with the process of Example 12 (inorganic base).

Example 14-22

Preparation of Compound of Formula XIV (G=OBn) from Compound of Formula XI (Y=4-chlorophenyl): Using essentially the same procedure as in example 12, the compound of Formula XIV (G=OBn) was prepared from the compound of Formula XI (Y=4-chlorophenyl, S/R ratio: 96.4/3.6) at different temperature and in different solvents. ACN: acetonitrile; NMP: N-methylpyrrolidinone.

| Example | Solvent | Temp. (° C.) | Yield % | Product (RS/SS) |
|---|---|---|---|---|
| 14 | NMP | 80 | 44.7 | 10.7 |
| 15 | NMP | 90 | 41.1 | 11.6 |
| 16 | NMP | 100 | 33.3 | 12.8 |
| 17 | toluene | 80 | 69.2 | 7.0 |
| 18 | toluene | 100 | 68.5 | 8.5 |
| 19 | 1:1:1 ACN/toluene/NMP | 80 | 58.1 | 6.6 |
| 20 | 1:1 ACN/NMP | 80 | 54.8 | 8.3 |
| 21 | ACN | 80 | 76.1 | 5.4 |
| 22 | 1:1 toluene/NMP | 80 | 48.4 | 6.1 |

Example 23

Preparation of Compound of Formula XIV (G=OBn) from Compound of Formula XI (Y=4-chlorophenyl): Using essentially the same procedure as in example 12 except that trisodium phosphate was used as the base, the compound of Formula XIV (G=OBn) was prepared from the compound of Formula XI (Y=4-chlorophenyl, S/R ratio: 95.8/4.2). Yield: 83%. Diastereomeric ratio (RS/SS: 95.2/4.8).

Example 24

Preparation of Compound of Formula XIV (G=OBn) from Compound of Formula XI (Y=4-chlorophenyl): Using essentially the same procedure as in example 12 except that calcium carbonate was used as the base, the compound of Formula XIV (G=OBn) was prepared from the compound of Formula XI (Y=4-chlorophenyl, S/R ratio: 95.8/4.2). Yield: 48%. Diastereomeric ratio (RS/SS: 88.7/11.3).

Example 25-31

Preparation of Compounds of Formula XIV from Compound of Formula XI: Compounds of Formula XIV were prepared using similar procedures to Example 12.

| Example | G | Y | Time (h) | Yield % | Sulfonate S/R ratio | Product RS/SS ratio |
|---|---|---|---|---|---|---|
| 25 | Me | 4-Chlorophenyl | 24 | 50 | 96.4/3.6 | 94.7/5.3 |
| 26 | CF$_3$ | 4-Chlorophenyl | 65 | 62 | 96.4/3.6 | 94.5/5.5 |
| 27 | Ph | 4-Chlorophenyl | 17 | 75 | 96.4/3.6 | 95.2/4.8 |
| 28 | EtO | 4-Chlorophenyl | 20 | 88 | 96.4/3.6 | 96.2/3.8 |
| 29 | t-BuO | 4-Chlorophenyl | 19 | 87 | 98.6/1.4 | 96.1/3.9 |
| 30 | t-BuO | Phenyl | 34 | 90 (conversion) | 95.8/4.2 | 93.0/7.0 |
| 31 | t-BuO | Methyl | 96 | 87 | 98.6/1.4 | 95.6/4.4 |

Physical and spectral data for compounds of Formula XIV:

G=Me (Example 25): light brown oil, $^1$H NMR (CDCl$_3$): 7.48 (m, 4H), 3.97 (m, 1H), 2.95-3.80 (m, 7H), 3.27, 3.25 (split S, 3H), 2.42 (m, 1H), 2.24 (m, 1H), 2.02, 1.99 (split s, 3H), 1.08 (split d, J=6.3 Hz, 3H).

G=CF$_3$ (Example 26): white solid, $^1$H NMR (CDCl$_3$): 7.61 (dd, J$_1$=8.3 Hz, J$_2$=2.4 Hz, 2H), 7.54 (d, J=8.1 Hz, 2H), 4.08 (m, 1H), 3.72 (m, 3H), 3.45 (m, 3H), 3.36, 3.35 (split s, 3H), 3.27 (m, 1H), 2.58 (m, 1H), 2.42 (m, 1H), 1.20 (d, J=6.3 Hz, 3H).

G=Ph (Example 27): off-white solid, $^1$H NMR (CDCl$_3$): 7.55 (br m, 4H), 7.40 (br s, 5H), 3.62-4.20 (br m, 4H), 3.00-3.62 (br m, 4H), 3.35 (br s, 3H), 2.45 (br m, 2H), 1.26, 1.09 (split br s, 3H).

G=OEt (Example 28): pale yellow oil. $^1$H NMR (CDCl$_3$): 7.52 (m, 4H), 4.09 (q, J=7.0 Hz, 2H), 4.01 (br s, 1H), 3.68 (m, 2H), 3.59 (br s, 1H), 3.38 (m, 1H), 3.29 (s, 3H), 3.15 (m, 2H), 3.06 (m, 1H), 2.42 (m, 1H), 2.23 (m, 1H), 1.21 (t, J=6.9 Hz, 3H), 1.11 (d, J=6.1 Hz, 3H).

G=Ot-Bu (Example 29): white solid, $^1$H NMR (CDCl$_3$): 7.50 (m, 4H), 3.95 (br s, 1H), 3.64 (m, 2H), 3.48 (brs, 1H), 3.28 (brs, 1H), 3.26 (s, 3H), 3.10 (br s, 2H), 3.01 (m, 1H), 2.37 (m, 1H), 2.18 (m, 1H), 1.38 (s, 9H), 1.06 (d, J=6.2 Hz, 3H).

Example 32

Conversion of the Compound of Formula XIV (G=OBn) into the Compound of Formula VIII and then to its Tartrate

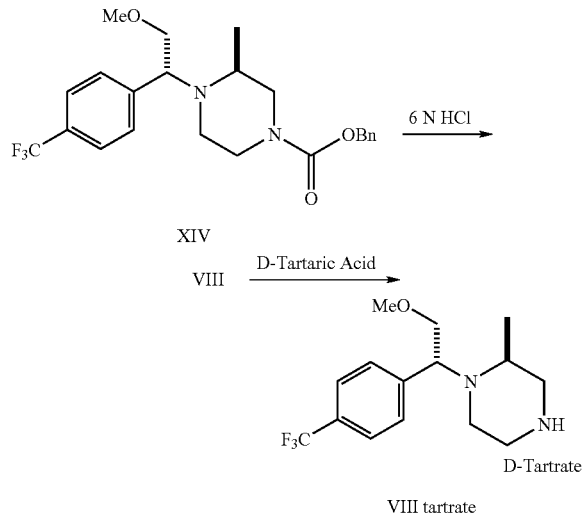

The compound of Formula XIV (G=OBn) (18.7 g) was heated in 6 N HCl (60 mL) for 1 h at 95-100° C. and cooled. The resulting mixture was washed with toluene twice and basified with sodium hydroxide to pH>13. The basic mixture was extracted with toluene twice and back-washed with water once. The organic layer was concentrated to give an oil. HPLC analysis showed 12.8 g free base (99% yield) of the compound of Formula VIII. Pure free base (clear oil) was obtained after flash column chromatography. $^1$H NMR (CDCl$_3$): 7.58 (s, 4H), 4.16 (t, J=5.7 Hz, 1H), 3.80 (m, 2H), 3.38 (s, 3H), 3.00 (m, 2H), 2.78 (m, 1H), 2.64 (m, 2H), 2.46 (m, 1H), 2.31 (m, 1H), 1.73 (brs, 1H), 1.18 (d, J=6.3 Hz, 3H).

To a solution of D-tartaric acid (7.6 g) in 135 mL methanol was added the above free base in 35 mL toluene at 55-65° C. over 1 h. The resulting slurry was heated at 55-65° C. for 1 h and cooled slowly to 0° C. The solids were filtered, washed with isopropanol (70 ML), and dried at 50-55° C. under vacuum to yield the tartrate of the compound of Formula VIII. White solid (m.p.: 209.7° C., 17.7 g, 92% yield). $^1$H NMR (D$_2$O): 7.60 (d, J=8.2 Hz, 2H), 7.49 (d, J=8.2 Hz, 2H), 4.32 (s, 2H), 4.27 (t, J=5.8, 1H), 3.84 (m, 2H), 3.38 (m, 1H), 3.25 (dd, J$_1$=13 Hz, J$_2$=3.0 Hz, 1H), 3.20 (s, 3H), 3.09 (m, 1H), 2.86 (m, 3H), 2.68 (m, 1H), 1.21 (d, J=6.5 Hz, 3H).

Example 33

Preparation of Compound of Formula VIII from Compound of Formula XIV (G=OEt) under Basic Conditions

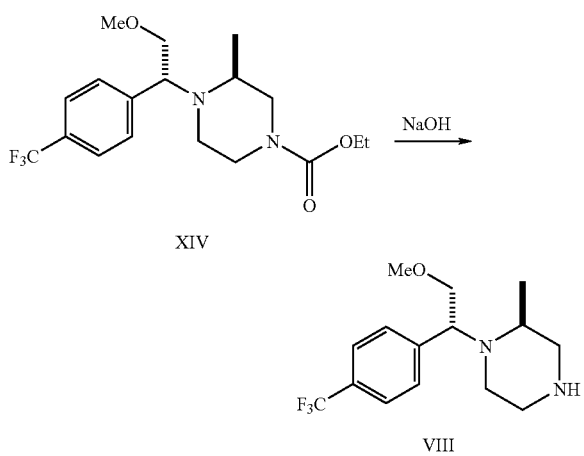

The compound of Formula XIV (G=OEt) (16.5 g) was heated with NaOH (17 g, 50% solution) in ethanol (50 mL) at reflux for 24 h, during which time period, additional NaOH (17 g, 50% solution) and ethanol (50 mL) were added. Upon cooling, water was added and the mixture was concentrated under vacuum. The resulting aqueous mixture was extracted with toluene twice and back-washed with water once. The organic layer was concentrated to give an oil. HPLC analysis showed 12.4 g compound of Formula VIII (93% yield).

Example 34

Preparation of the compound of Formula XVI: This was performed by the following two step reaction, following the procedure described in Baroudy et al, WO 00/66558 (published Nov. 9, 2000):

Step 1: A solution of 4-trifluoromethyl acetophenone (1.88 g; 10 mmol, from Aldrich Chemical Company, Milwaukee, Wis.) in dry THF (10 ml) was cooled in an ice bath and treated with solid (S)-2-methyl oxaborolidine (0.54 g; 2 mmol, from Callery Chemical Company, Evans City, Pa.). After 10 min., a solution of 2M borane-methyl sulfide complex (3 ml; 6 mmol) in THF was added dropwise over 5 min. Thin Layer Chromatography ("TLC") at the end of 30 min. showed that the starting material had been converted to a more polar product. The reaction was quenched with about 5 ml of CH$_3$OH carefully until effervescence stopped; the volatiles were removed in vacuo. The residue was dissolved in CH$_2$Cl$_2$ and washed with 1N HCl, water, 10% NaHCO$_3$ solution and brine. Concentration in vacuo gave 2 g of a yellow gum. Flash silica gel chromatography (FSGC) using 10-20% EtOAc in hexanes furnished the desired chiral alcohol (1.6 g; 84%) as a colorless oil. TLC: R$_f$=0.6 in 25% EtOAc:hexanes.

Step 2: To a solution of the product of step 1 (1.55 g; 8.16 mmol) in 10 ml of $CH_2Cl_2$ cooled in an ice bath were added $Et_3N$ (2.3 ml; 16.32 mmol) and $CH_3SO_2Cl$ (0.87 ml; 10.6 mmol) to form a turbid white solution. The reaction was quenched with water and the organic product was extracted with $CH_2Cl_2$, washing with water, 1N HCl, 10% $NaHCO_3$ solution and brine. Concentration in vacuo gave the chiral mesylate (2.1 g; 96%) as a pale yellow oil. TLC $R_f$=0.6 in 25% EtOAc:hexanes.

Example 35

Preparation of the compound of Formula XVII: This was also prepared, following the procedure described in Baroudy et al, WO 00/66558 (published Nov. 9, 2000):

The N—BOC protected 2(S)-methyl piperazine (formula XVI) (1.56 g; 7.8 mmol—prepared from the reaction of commercial 2(S)-methyl piperazine (from Deepwater Chemicals) with N-(tert-butoxy-carbonyloxy)phthalimide) (from Aldrich Chemical Company) and 2,2,6,6-tetramethyl piperidine (1.34 ml; 8 mmol).

Example 36

Preparation of the compound of Formula XV (using $K_2CO_3$ as base): 13.2 kg (0.52×) milled potassium carbonate, 52.55 kg of a solution of the compound of Formula XVII containing 19.18 kg (0.76×) of the active the compound of Formula XVII in acetonitrile, and 75.45 kg of a solution of the compound of Formula XVI containing 25.4 kg (1.0×) of the compound of Formula XVI in acetonitrile were charged to a 100 gallon glass lined reactor equipped with a thermocouple, $N_2$ inlet and feed tank. 80 liters (3.15×) of dry acetonitrile were charged to adjust the total batch volume to about 200 liters (8.0×). With agitation, the slurry was heated to a temperature between 80 and 90° C. over a period of about 30 minutes. The batch was agitated for about 16 hours at this temperature range. The temperature was adjusted to about 20 to 30° C. The batch was sampled for analysis. The batch was considered complete when a maximum of 5.0% of the compound of formula the compound of Formula XVI remained by HPLC. Slowly 51 L (2.0×) water was charged to quench the reaction. The mixture was agitated for about 15 minutes and the batch allowed to settle. The bottom aqueous layer was split off. The upper, organic, layer was concentrated under vacuum to afford a batch volume of 51 liters (2.0×) at a temperature below 70° C. The temperature was adjusted to about 20 to 30° C. 168 liters (6.6×) toluene and 99 liters (3.9×) water were charged to the batch. The mixture was agitated for about 15 minutes and the batch allowed to settle. The upper, organic, layer was concentrated under vacuum at below 80° C. to afford a volume of about 51 liters (2.0)×. The temperature was adjusted to about 20 to 30° C. to afford the compound of formula the compound of Formula XV in 81% overall yield from the compound of formula (XVI) and a diastereomeric ratio (dr) of 95.6/4.4 S,S/R,S as a solution in toluene.

Example 37

Preparation of the compound of Formula XV (using $NaHCO_3$ as base): 3.13 g (0.63×) sodium bicarbonate, 4.67 g an oil containing 3.73 g (0.75×) of the active the compound of Formula XVII, 5.21 g an oil containing 5.0 g (1.0×) of the compound of Formula XVI, and 30 mL (6.0×) dry acetonitrile were charged in a 125 mL 3 necked round bottom flask equipped with a thermometer and reflux condenser. With agitation, the slurry was heated to a temperature between 90 and 95° C. over a period of 30 minutes. The batch was agitated for about 19 hours at this temperature range. The temperature was adjusted to about 20 to 30° C. The batch was sampled for analysis. The batch was considered complete when a maximum of 5.0% of the compound of Formula XVI remained by HPLC. The slurry was filtered to afford the compound of Formula XV in 83% overall yield from the compound of Formula XVI and a dr of 94.8/5.2 S,S/R,S as a solution in acetonitrile.

Example 38

Preparation of the compound of Formula XV (using $Na_2CO_3$ as base): 1.54 g (0.51×) sodium carbonate, 2.87 g an oil containing 2.24 g (0.75×) of the compound of Formula XVII, 3.07 g an oil containing 3.0 g (1.0×) of the compound of Formula XVI, and 15 mL (5.0×) dry acetonitrile were charged in a 125 mL 3 necked round bottom flask equipped with a thermometer and reflux condenser. With agitation, the slurry was heated to a temperature between 95 and 100° C. over a period of 20 minutes. The batch was agitated for about 24 hours at this temperature range. The temperature was adjusted to about 20 to 30° C. The batch was sampled for analysis. The batch was considered complete when a maximum of 5.0% of the compound of formula XVI remained by HPLC. The slurry was filtered to afford the compound of formula XV in 83% overall yield from the compound of formula XVII and a dr of 95.5/4.5 S,S/R/S as a solution in acetonitrile.

Example 39

Preparation of the compound of Formula XV (using $NaHCO_3$ as base): 3.1 g (0.64×) sodium bicarbonate, 5.13 g an oil containing 4.11 g (0.84×) of the active compound of formula XVII, 5.0 g an oil containing 4.88 g (1.0×) of the compound of formula XVI, and 30 mL (6.2×) dry acetonitrile were charged in a 125 mL 3 necked round bottom flask equipped with a thermometer and reflux condenser. With agitation, the slurry was heated to a temperature between 90 and 95° C. over a period of 20 minutes. The batch was agitated for about 8 hours at this temperature range. The temperature was adjusted to about 20 to 30° C. The batch was sampled for analysis. The batch was considered complete when a maximum of 5.0% of the compound of formula XVI remained by HPLC. The slurry was filtered to afford the compound of formula XV in 86% overall yield from the compound of formula XVI and a dr of 94.0/6.0 S,S/R/S as a solution in acetonitrile.

Example 40

Preparation of the compound of Formula XV (using $K_2CO_3$ as base): 10.31 g (0.52×) powdered potassium carbonate, and 18.69 g an oil containing 14.93 g (0.75×) of the active compound of formula XVII, and 70 mls (3.5×) dry acetonitrile were charged in a 500 mL 3 necked round bottom flask equipped with a thermometer and a reflux condenser. With agitation, the slurry was heated to a temperature between 90 and 95° C. over a period of 20 minutes. Slowly, over a period of 5 hours, a solution of 20.49 g an oil containing 20.0 g (1.0×) active of the compound of formula XVI dissolved to a total volume of 50 mLs (2.5×) in dry acetonitrile were charged while maintaining the batch temperature in a range of 90 to 95° C. After the addition has been completed, the batch was agitated for an additional 14 hours at this temperature range. The temperature was adjusted to about 20 to 30° C. The batch was sampled for analysis. The batch was considered complete when a maximum of 5.0% of the compound of formula XVI remained by HPLC. The slurry was filtered to afford the compound of formula XV in 82% overall yield from the compound of formula XVI and a dr of 94.7/5.3 S,S/R,S as a solution in acetonitrile.

Example 41

Preparation of the compound of Formula XV (using organic base): 1.13 g an oil containing 1.00 g (0.75×) of the active compound of formula XVII, 1.38 g XVI oil containing 1.34 g (1.0×) active of the compound of formula XVI, 0.88 ml (0.66×, 1.3 molar equivalents) 2,6 dimethylpiperidine and 5 mL (3.7×) dry acetonitrile were charged in a 50 mL 3 necked round bottom flask equipped with a thermometer and reflux condenser. With agitation, the slurry was heated to a temperature between 90 and 95° C. over a period of 20 minutes. The batch was agitated for about 8 hours at this temperature range. The temperature was adjusted to about 20 to 30° C. The batch was sampled for analysis. The batch was considered complete when a maximum of 5.0% of the compound of formula XVI remained by HPLC. The process afforded the compound of formula XV in 76.5% overall yield from the compound of formula XVI and a dr of 82.6/17.4 S,S/R,S as a solution in acetonitrile.

Example 42

Preparation of the compound of Formula XV (using organic base): 1.13 g of an oil containing 1.00 g (0.75×) of the active compound of formula XVII, 1.38 g of an oil containing 1.34 g (1.0×) active of the compound of formula XVI, 1.13 ml (0.84×, 1.3 molar equivalents) N,N-diisopropylethylamine and 5 mL (3.7×) dry acetonitrile were charged in a 50 mL 3 necked round bottom flask equipped with a thermometer and reflux condenser. With agitation, the slurry was heated to a temperature between 90 and 95° C. over a period of 20 minutes. The batch was agitated for about 8 hours at this temperature range. The temperature was adjusted to about 20 to 30° C. The batch was sampled for analysis. The batch was considered complete when a maximum of 5.0% of the compound of formula XVI remained by HPLC. The process afforded the compound of formula XV in 65% overall yield from the compound of formula XVI and a dr of 78.5/21.5 S,S/R,S as a solution in acetonitrile.

Example 43

Preparation of the compound of Formula XV (using organic base): 1.13 g of an oil containing 1.00 g (0.75×) of the active compound of formula XVII, 1.38 g of an oil containing 1.34 g (1.0×) active of the compound of formula XVI, 1.13 ml (0.84×, 1.6 molar equivalents) triethylamine and 5 mL (3.7×) dry acetonitrile were charged in a 50 mL 3 necked round bottom flask equipped with a thermometer and reflux condenser. With agitation, the slurry was heated to a temperature between 90 and 95° C. over a period of 20 minutes. The batch was agitated for about 8 hours at this temperature range. The temperature was adjusted to about 20 to 30° C. The batch was sampled for analysis. The batch was considered complete when a maximum of 5.0% of the compound of formula XVI remained by HPLC. The process afforded the compound of formula XV in 60.5% overall yield from the compound of formula XVI and a dr of 78.8/21.2 S,S/R,S as a solution in acetonitrile.

Example 44

Conversion of the compound of Formula XV into the Compound of Formula VIII (X=CF$_3$ and Z=Me) free base): A solution of the compound of Formula XV (114.52 g, 0.308 moles) in toluene (total volume 760 mls (6.6×) from the previous step was charged to a 2 liter 3 necked round bottom flask with mechanical stirring. With stirring, the solution was chilled to an internal temperature between 0 and 10° C. A solution of concentrated hydrochloric acid (230 mls, 2.74 moles, 8.9 equivalents) was charged slowly over about 30 mins while maintaining the internal temperature less than 15° C. After the addition was complete, the batch was raised to a temperature between 20 and 25° C. and agitated for about 1.5 hours until no more starting material remained by HPLC. The 2 phase solution was allowed to settle for about 10 minutes and the phases were allowed to separate. The lower aqueous layer containing the batch was returned to the reaction vessel and was cooled to a temperature between 0 and 5° C. with stirring. The pH of the solution was adjusted to >12.0 by the slow addition of 290 ml (2.5×) 25% aqueous w/v NaOH over about 1 hour. The aqueous slurry was extracted twice with 250 ml (2.2×) toluene. The organic layers were combined and distilled under vacuum to a low volume. An additional 300 mls (2.6×) of toluene was added and the solution was again concentrated under vacuum to a low volume. The compound of Formula VIII (wherein X=CF$_3$ and Z=methyl) was obtained (85.2 g, 101.6% by internal standard). This could be converted to a desired salt such as, for example, tartrate, as exemplified in Example 32 above.

As stated above, it will be apparent to those skilled in the art that many modifications, variations and alterations to the present disclosure, both to materials, methods and reaction conditions, may be practiced. Additionally, while the various steps in the inventive processes have been described herein with certain stereochemistry, it will be apparent to those skilled in the art that the processes would still work if the configurations of the piperazine and the alkylating reagent are permutated. All such modifications, variations, alterations and permutations are intended to be within the spirit and scope of the present invention.

What is claimed is:

1. A process to prepare a compound of Formula XIV,

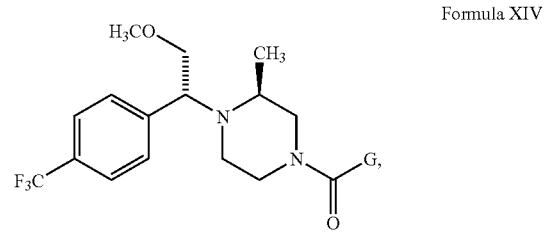

where G is selected from the group consisting of alkyl, halogenated alkyl, alkoxy, aryl aryloxy and arylalkoxy, by reacting a compound of Formula XI,

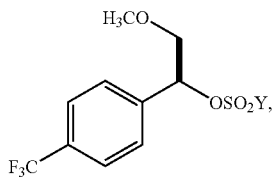

where Y is selected from the group consisting of alkyl, halogenated alkyl, or aryl with said aryl being optionally substituted with alkyl, nitro or halogen,
with a compound of Formula X,

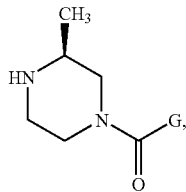

in the presence of an inorganic catalyst in a solvent, wherein said compound of Formula XIV forms in at (east 50% yields with at least about a 2:1 ratio of R,S stereochemistry to S,S stereochemistry respectively.

2. The process of claim 1, wherein Y is methyl, tolyl or 4-chlorophenyl, and G is selected from the group consisting of methyl, ethyl, trifluoromethyl, phenyl, ethoxy, t-butoxy and benzyloxy.

3. The process of claim 1, wherein said solvent is a hydrocarbon, nitrile or mixtures of two or more thereof, the catalyst is selected from the group consisting of a carbonate, bicarbonate, phosphate, sulfite and mixtures thereof, and said ratio of stereochemistry is at least about 3:1.

4. The process of claim 3, wherein said solvent is a mixture of toluene and acetonitrile and the catalyst is selected from the group consisting of $K_2CO_3$, $NaHCO_3$, $Na_3PO_4$, $CaCO_3$, and $K_2SO_3$.

5. The process of claim 1, wherein said compound of formula XIV is further reacted with an acid to form the compound of the formula:

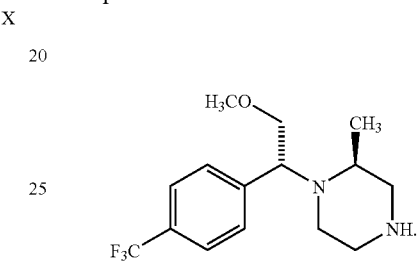

* * * * *